United States Patent [19]
Bonewitz et al.

[11] Patent Number: 5,926,268
[45] Date of Patent: Jul. 20, 1999

[54] SYSTEM AND METHOD FOR STRESS DETECTION IN A MOLDED CONTAINER

[75] Inventors: Manuel Bonewitz; Bozidar Kosta; Richard Parniawski, all of Clearwater, Fla.

[73] Assignee: Inex, Inc., Clearwater, Fla.

[21] Appl. No.: 08/868,715

[22] Filed: Jun. 4, 1997

Related U.S. Application Data

[60] Provisional application No. 60/018,970, Jun. 4, 1996.

[51] Int. Cl.$^6$ ................................................. G01N 21/00
[52] U.S. Cl. ........................... 356/240; 356/390; 356/370
[58] Field of Search ................................. 356/237, 240, 356/390, 32–34, 364, 366–367, 370, 428, 72; 250/223 B; 382/142; 348/127; 209/526, 576–577, 579, 938–939

[56] References Cited

U.S. PATENT DOCUMENTS

| | | | |
|---|---|---|---|
| 3,328,000 | 6/1967 | Rottmann | 250/223 B |
| 3,356,212 | 12/1967 | Landin . | |
| 3,716,136 | 2/1973 | Birner et al. . | |
| 3,963,348 | 6/1976 | Nakatani et al. . | |
| 4,021,122 | 5/1977 | Krenmayr | 356/240 |
| 4,026,656 | 5/1977 | Kusz et al. | 356/51 |
| 4,064,534 | 12/1977 | Chen et al. | 358/107 |
| 4,074,938 | 2/1978 | Taylor . | |
| 4,082,463 | 4/1978 | Dehait et al. . | |
| 4,097,158 | 6/1978 | Dehait . | |
| 4,136,930 | 1/1979 | Gomm et al. | 358/106 |
| 4,175,236 | 11/1979 | Juvinall | 250/566 |
| 4,230,266 | 10/1980 | Juvinall | 235/490 |
| 4,283,145 | 8/1981 | Miyazawa | 356/364 |
| 4,376,951 | 3/1983 | Miyazawa | 356/240 |
| 4,391,373 | 7/1983 | Wiggins | 209/526 |
| 4,399,357 | 8/1983 | Dorf et al. | 250/223 B |
| 4,459,487 | 7/1984 | Leser | 250/560 |
| 4,492,477 | 1/1985 | Leser | 356/430 |
| 4,509,081 | 4/1985 | Peyton et al. | 358/225 |
| 4,644,151 | 2/1987 | Juvinall | 250/223 B |
| 4,691,231 | 9/1987 | Fitzmorris et al. | 358/106 |
| 4,694,158 | 9/1987 | Leser | 250/223 B |
| 4,731,649 | 3/1988 | Chang et al. | 358/106 |
| 4,736,851 | 4/1988 | Ricros et al. | 209/524 |
| 4,750,035 | 6/1988 | Chang et al. | 358/106 |
| 4,801,319 | 1/1989 | Rugaber et al. | 65/29 |
| 4,874,940 | 10/1989 | McMeekin et al. | 250/223 B |
| 4,906,098 | 3/1990 | Thomas et al. | 356/376 |
| 4,914,289 | 4/1990 | Nguyen et al. | 250/223 B |
| 4,915,237 | 4/1990 | Chang et al. | 209/524 |
| 4,945,228 | 7/1990 | Juvinall et al. | 250/223 B |
| 5,090,576 | 2/1992 | Menten | 209/587 |
| 5,095,204 | 3/1992 | Novini | 356/240 |
| 5,202,932 | 4/1993 | Cambier et al. . | |
| 5,214,713 | 5/1993 | Juvinall . | |
| 5,243,184 | 9/1993 | Fukuchi et al. | 250/223 R |
| 5,256,871 | 10/1993 | Baldwin | 250/223 B |
| 5,258,611 | 11/1993 | Leser | 250/223 B |
| 5,260,780 | 11/1993 | Staudt, III | 358/107 |
| 5,267,033 | 11/1993 | Hoshino | 358/101 |
| 5,270,535 | 12/1993 | Leser | 250/223 B |
| 5,405,015 | 4/1995 | Bhatia et al. | 209/524 |
| 5,437,702 | 8/1995 | Burns et al. | 65/29.12 |
| 5,442,446 | 8/1995 | Gerber et al. | 356/428 |
| 5,486,692 | 1/1996 | Baldwin | 250/223 B |
| 5,499,718 | 3/1996 | Bhatia et al. | 209/524 |

FOREIGN PATENT DOCUMENTS

| | | |
|---|---|---|
| 0 415 154 | 4/1995 | European Pat. Off. . |
| 2 437 616 | 9/1979 | France . |
| 2 475 424 | 2/1980 | France . |
| 29 10 516 | 9/1980 | Germany . |

*Primary Examiner*—Robert Kim
*Attorney, Agent, or Firm*—Senniger, Powers, Leavitt & Roedel

[57] ABSTRACT

System and method for inspecting a container for defects. A first polarizer positioned between a light source and the container polarizes light provided by the light source for illuminating the container. A second polarizer positioned between the container and a camera polarizes the light transmitted through the container to the camera. As positioned, the axes of transmission of the first and second polarizers are non-parallel relative to each other. An image processor processes an image generated by the camera as a function of an optical characteristic of the image to detect defects in the container.

36 Claims, 9 Drawing Sheets

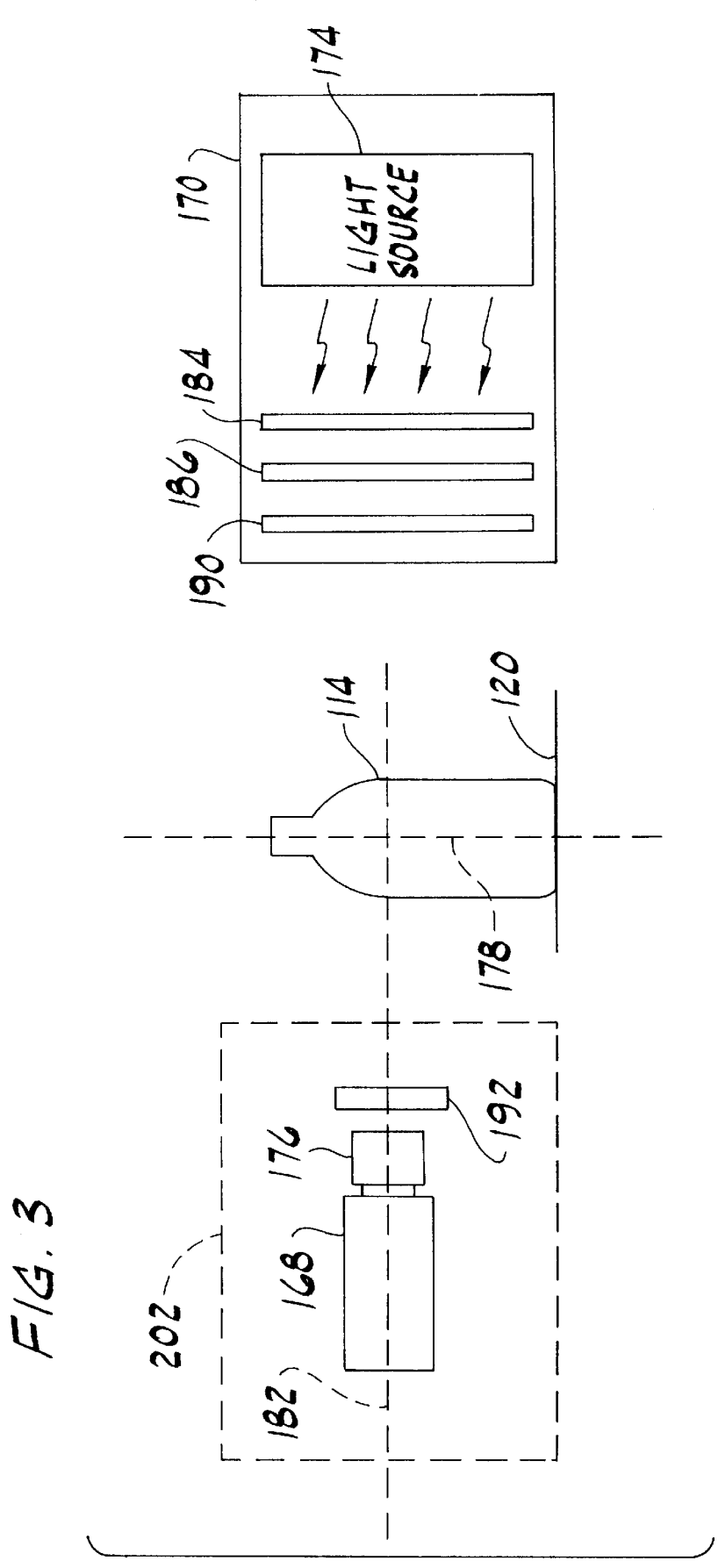

SYSTEM AND METHOD FOR STRESS DETECTION IN A MOLDED CONTAINER

CROSS-REFERENCE TO RELATED APPLICATION

This application claims the benefit of Provisional application Ser. No. 60/018,970, filed Jun. 4, 1996, the entire disclosure of which is incorporated herein by reference.

BACKGROUND OF THE INVENTION

The invention relates generally to container inspection systems and, particularly, to a vision system for identifying stress-related defects in a molded container.

Container molding machines, referred to in the industry as individual section (IS) machines, are used to form containers, such as glass bottles and jars. Typically, an IS machine has a number of sections, each section having multiple cavities or molds, in which molten glass is formed into the desired container shape. After forming, a conveyor or the like moves the containers through a lehr which anneals the glass by subjecting the containers to stress-relieving temperatures. During the forming and annealing process, defects (e.g., improper annealing, embedded foreign objects, variations in glass density, or other anomalies) may occur which cause stress in the defective container. For this reason, an accurate and reliable inspection system is needed for identifying containers that have stress defects.

Further, many of these defects may be corrected during the manufacturing process to minimize the number of defective containers that are formed. Therefore, such an inspection system which provides feedback to the container molding machine and/or lehr is desired to correct defects in subsequently formed containers.

SUMMARY OF THE INVENTION

Among the several objects of this invention may be noted the provision of a system and method for inspecting a molded container which overcomes the disadvantageous conditions described above; the provision of such system and method which permits use with an automated inspection system; the provision of such system and method which permits use with an automated container handling apparatus; the provision of such system and method which permits detection of stress-related defects in the container; and the provision of such system and method which is economically feasible and commercially practical.

Briefly described, a system embodying aspects of the invention is for inspecting a container for stress defects. The system includes a light source for illuminating the container and a camera for generating an image of the illuminated container. A first polarizer positioned between the light source and the container polarizes the light illuminating the container and a second polarizer positioned between the container and the camera polarizes the light transmitted through the container before the camera generates the image. As positioned, the axes of transmission of the first and second polarizers are non-parallel relative to each other. The image generated by the camera has a plurality of pixels each with a value representative of an optical characteristic of the image. The system further includes an image processor for processing the image generated by the camera as a function of the pixel values to detect edges in the image which correspond to defects in the container.

Another embodiment of the invention is directed to a method of inspecting a container for stress defects. The method includes the steps of positioning the container between a light source and a camera, positioning a first polarizer between the light source and the container and positioning a second polarizer between the container and the camera. As positioned, the axes of transmission of the first and second polarizers are non-parallel relative to each other. The method also includes illuminating the container with the light source, polarizing the light illuminating the container with the first polarizer and polarizing the light transmitted through the container with the second polarizer. The method also includes the step of generating an image of the container with the rev camera. The image generated by the camera has a plurality of pixels each with a value representative of an optical characteristic of the image. The method further includes processing the image as a function of the pixel values to detect edges in the image which correspond to defects in the container.

Other objects and features will be in part apparent and in part pointed out hereinafter.

BRIEF DESCRIPTION OF THE DRAWINGS

FIG. 3 is a diagrammatic view of a container to be inspected in an inspection station of the system of FIG. 1 according to a preferred embodiment of the invention.

Corresponding reference characters indicate corresponding parts through the drawings.

DETAILED DESCRIPTION OF PREFERRED EMBODIMENTS

Figure 1:
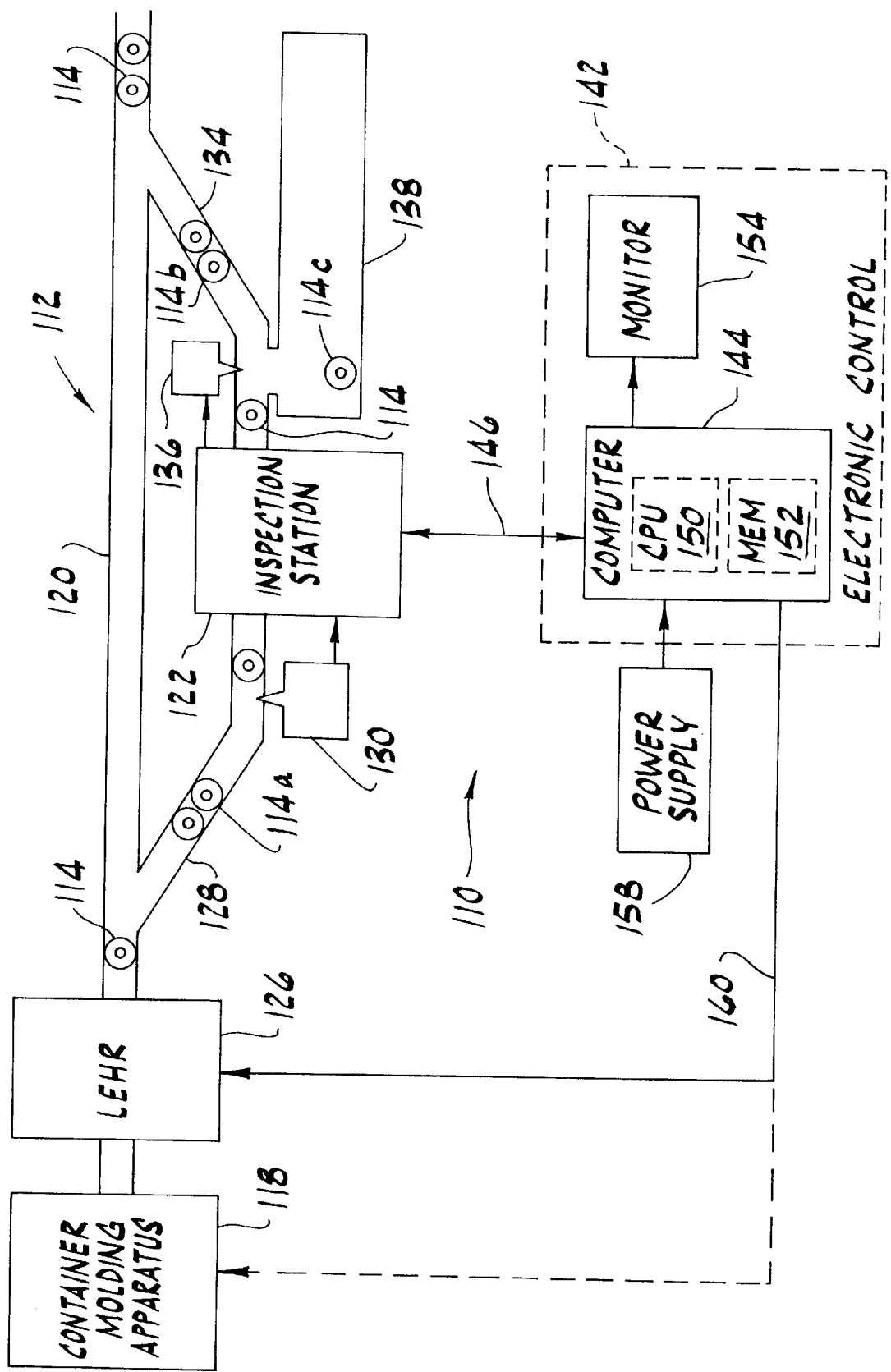
FIG. 1 is a block diagram of a system for inspecting containers according to a preferred embodiment of the invention in combination with a container handling apparatus transporting containers from a container molding apparatus to the system.

Referring now to the drawings, FIG. 1 illustrates a container inspection system 110 according to the present invention. In a preferred embodiment, the system 110 is for use with a container handling apparatus 112 that handles a plurality of containers 114, each formed by a container molding apparatus 118. For example, the container molding apparatus 118 comprises an individual section machine having a plurality of molds, or cavities, in which the containers 114 are formed from molten glass or other materials. This stage of glass manufacture is referred to as the hot end.

After forming and annealing, a main conveyor 120 of the container handling apparatus 112 delivers containers 114 to various other stations, such as an inspection station 122 for container inspection and/or mold number identification. The main conveyer 120 may be any standard container mover known to those skilled in the art, such as a horizontal belt conveyer or a channel through which containers 114 are pushed.

As described above, container molding apparatus 118 has a plurality of individual sections (e.g., sixteen sections), with each section having a plurality of molds (e.g., four molds). Such apparatus 118 is capable of producing containers 114 at a relatively high rate of speed (e.g., six hundred containers per minute). According to the invention, the speed of main conveyer 120 is preferably set to accommodate the relatively high rate of speed at which molding apparatus 118 produces containers 114. The inspection system 110 is also synchronized to this speed.

For glass container production, main conveyor 120 moves containers 114 from molding apparatus 118 through a lehr 126. The lehr 126 anneals the glass by subjecting containers 114 to stress-relieving temperatures. An infeed conveyor 128 then delivers containers 114 to the inspection station 122. In a preferred embodiment, system 110 inspects containers 114 for defects (e.g., improper annealing, embedded foreign objects, variations in glass density, or other anomalies causing stress).

It is to be understood that inspection system 110 may include means for inspecting containers 114 for characteristics other than stress-related defects. Such other inspection means may be housed within inspection station 122 or within a separate additional inspection station. For example, as is known in the container manufacturing industry, each container 114 will typically include an identifying pattern that identifies the particular mold of container molding apparatus 118 in which it originated. Preferably, inspection station 122 includes a mold number reader for identifying these identifying patterns. As an example, commonly assigned application Ser. No. 08/707,320 the entire disclosure of which is incorporated herein by reference, discloses a preferred mold number reading system.

Although container 114 is typically a molded glass bottle in the present application, system 110 advantageously performs stress detection for different types of containers. Further, it is to be understood that the principles of the invention may also be applied to containers manufactured by a variety of processes from a variety of materials such as glass or plastic.

Before containers 114 enter inspection station 122 a container separator 130 spaces them apart at regular intervals to facilitate the inspection process. For example, a finger wheel or star wheel apparatus having a plurality of fingers for engaging and separating containers 114 as they feed into inspection station 122 via the infeed conveyor 128 constitutes a suitable container separator 130. In this manner, container separator 130 ensures that containers 114 will be evenly spaced. Preferably, the fingers are adjustable to accommodate containers 114 of different size. A container 114a is shown on infeed container 128.

After inspection, an outfeed conveyor 134 returns containers 114 to main conveyor 120. A container 114b is shown on the outfeed conveyor 134. If any of containers 114 are found to be defective, a rejector 136 removes them from outfeed conveyor 134. The rejector 136 preferably comprises an air jet or mechanical ram that pushes the defective containers, such as a container 114c, from outfeed conveyor 134 to a reject accumulation conveyor 138 connected to outfeed conveyor 134. The reject accumulation conveyor 138 then collects each rejected container 114c for later disposal.

As shown in FIG. 1, containers 114 either travel through inspection station 122 or bypass it by remaining on main conveyor 120. Generally, all containers 114 are routed to inspection station 122 for inspection by system 110. However, it may be necessary on occasion to bypass system 110 to prepare for job changes or to perform other tasks such as routine maintenance. Thus, system 110 may include a diverting gate (not shown) for selectively diverting containers 114 from main conveyor 120 to infeed conveyor 128.

In addition to inspection station 122, system 110 has an electronic control 142 that includes a computer 144 communicating with inspection station 122 via line 146 (e.g., interface cables). For example, the computer 144 has a central processing unit 150 comprising an Intel® image processor, a general-type RISC processor programmed to perform image analysis, or like processor, and a memory 152, as well as the other circuits, for performing image acquisition and processing tasks. For example, system 110 employs visual imaging techniques which extract information regarding variations in shading to detect the presence of production defects, contamination and/or damage (e.g., improper annealing, embedded foreign objects, variations in glass density, or other anomalies causing stress).

A monitor 154 displays information regarding the inspection and a power supply 158 provides power to each component of system 110. Inspection system 110 also communicates with lehr 126 and/or container molding apparatus 118 via line 160. If a consistent failure or undesirable trend exists, and this failure or trend is due to the annealing process, inspection system 110 informs the automated control of lehr 126 (or its operator) to either correct the problem or shut down the molding process to diagnose the problem more fully. In a preferred embodiment of the invention, computer 144 executes a series of diagnostic routines stored in its memory 152. By executing these routines, computer 144 is able to determine the cause of the detected defects and prescribe corrective actions to prevent the defects from recurring in containers 114 subsequently produced by molding apparatus 118.

Figure 2:
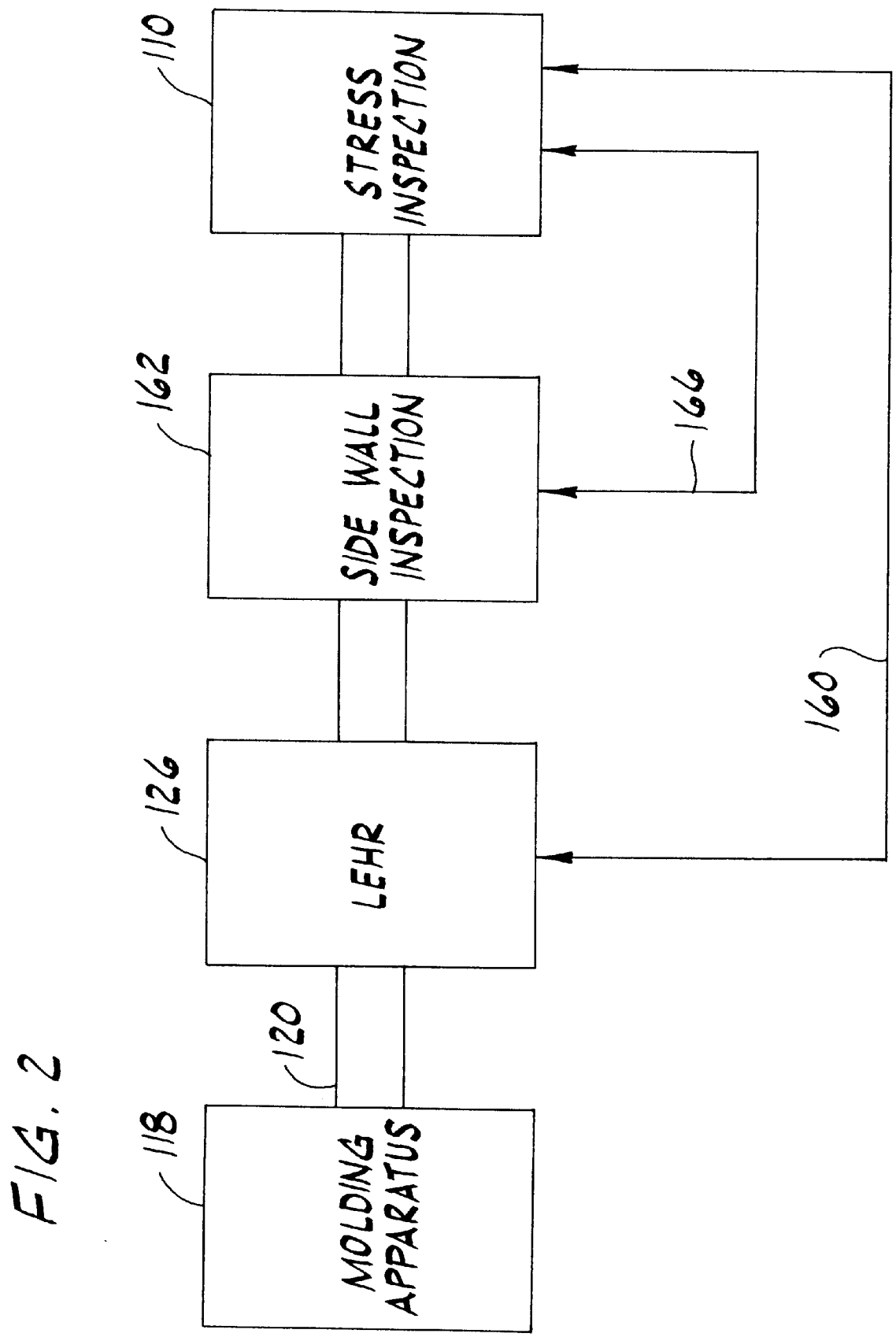
FIG. 2 is a block diagram of the system of FIG. 1 according to another preferred embodiment of the invention.

FIG. 2 shows the stress detection inspection system 110 in a preferred in-line configuration. In this embodiment, the inspection station 122 of system 110 is located in-line with main conveyor 120 such that main conveyor 120 constitutes both infeed conveyor 128 and outfeed conveyor 134. FIG. 2 also illustrates a data link between system 110 and another inspection system 162, such as a side wall inspection system. Using inspection system 110 in a closed loop manner with lehr 126 permits modification of the annealing process based on information from the stress inspection. A data link illustrated by line 166 permits the measurements from the stress inspection performed by system 110 to be correlated with the measurements from the other inspection performed by system 162. For clarity, the remaining description of the present invention will refer to the in-line configuration of FIG. 2.

FIG. 3 provides a diagram illustrating the interior of inspection station 122. As shown, a preferred electronic/optical imaging configuration for side wall stress detection includes a camera 168 and a diffuser/strobe assembly 170 positioned across from camera 168 for illuminating container 114. The diffuser/strobe assembly 170 has a light source 174 which flashes, or strobes, each time one of containers 114 passes through the imaging area (i.e., in the optical path of camera 168). The light source provides relatively even illumination from 400 nm to 1100 nm in wavelength. In the alternative, the light source 174 provides relatively constant, instead of pulsed, illumination depending on, for example, the density of glass of container 114.

In a preferred embodiment, the camera 168 is a high resolution CCD (charge-coupled device) video camera. One criteria for determining the specific type of camera to be used is the type of light source. For example, if light source 174 provides strobed or pulsed illumination, a frame reset CCD camera is preferred. On the other hand, if light source 174 provides relatively constant illumination, a shuttered CCD camera is preferred. Camera 168, which has a wide angle lens 176, generates an image of the side wall of container 114 as it passes in between diffuser/strobe assembly 170 and camera 168. In particular, container 114 has an axis of symmetry 178 and camera 168 has an optical axis 182 defined by the lens 176. According to the invention, camera 168 generates the image of container 114 approximately when the axes 178, 182 intersect. In other words, camera 168 generates an image of container 114 when it is approximately centered in front of camera 168. System 110 then utilizes visual imaging and computer analysis techniques to inspect empty containers 114 to detect the presence of production defects, contamination and/or damage. It is to be understood that the image of container 114 generated by camera 168 includes at least a portion of container 114 (e.g., a side wall portion) viewed from a particular angle.

Although container 114 is shown in a vertical or upright orientation, it is to be understood that this orientation is merely illustrative. System 110 inspects containers 114 without regard to their orientation so long as the relationship between camera 168 and the side wall portions of containers 114 is generally the same. Further, it is also contemplated that camera 168 may be positioned to receive reflected light rather than being in-line as shown in FIG. 3.

According to a preferred embodiment of the present invention, diffuser/strobe assembly 170 has several layers at the output of light source 174 for altering the light which illuminates container 114. In some applications, diffuser/strobe assembly 170 may include a diffuser mask (not shown) to focus the illumination in a smaller area. A layer of diffusion material, such as #254039001 available from F. J. Gray and Co., comprises a translucent diffuser lens 184 which distributes the light over the inspection area so that the portion of container 114 to be imaged is illuminated relatively evenly. Preferably, the diffuser lens 184 is larger than the container 114 under inspection. A next layer comprises a light control filter 186. The light control filter 186, also referred to as a louver, causes the light to propagate in a consistent direction which reduces glare from the edge or radius of container 114. Light control filter 186 is particularly useful during inspection of certain containers 114 due to the process by which they were formed or their diameter. In a preferred embodiment, light control filter 186 is embodied by a light control film #LCF-P AMBRO OB60 CLR GLS .032 12×30 Untrimmed, manufactured by 3M.

In addition to light control filter 186, diffuser/strobe assembly 170 includes a first polarizer 190. In this instance, the polarizer 190 is embodied by a linear polarizing filter positioned between light source 174 and container 114. Depending on the particular characteristics of container 114, however, it is contemplated that polarizer 190 may be a circular or elliptical polarizer. For example, a circular polarizer reduces glare from decorations and embossing. A suitable polarizer #HN385 is available from Polaroid. In a preferred embodiment of the invention, diffuser lens 184, light control filter 186 and polarizer 90 are positioned relative to light source 174 as shown in FIG. 3.

System 110 also includes a second polarizer 192 for polarizing the light transmitted through container 114 to camera 168. As before, the second polarizer 192 is embodied by a linear polarizing filter. Polarizer 192 may also be embodied by a circular or elliptical polarizer. As with the first polarizer 190, polarizer 192 is also preferably embodied by a #HN385 polarizer from Polaroid.

Polarized light highlights stress regions in glass bottles. In this instance, a preferred imaging configuration of the invention has container 114 placed between polarizer 190 and polarizer 192. As is well known in the art, a polarizer has an axis of transmission. Generally, light with an orientation parallel to the transmission axis is transmitted whereas light with an orientation perpendicular to the transmission axis is absorbed. Preferably, the transmission axes of polarizers 190, 192 are an angle $\theta \approx 90°$ with respect to one another. By orienting polarizers 190, 192 so that their transmission axes are not in the same direction, polarizer 190 first polarizes the light from light source 174 and then polarizer 192 blocks the polarized light. Thus, the resulting image of a non-stressed container 114 is essentially black. However, if the container 114 under inspections has regions of stress, these regions affect the polarization of the light. According to the invention, light passes through the second polarizer 192 where the polarization by polarizer 190 has been altered and, thus, defective or stressed areas in container 114 appear bright in the image generated by camera 168. As such, defects in container 114 which would have otherwise been essentially invisible are now visible in the image generated by camera 168. It is to understood that the transmission axes need not be perpendicular for defects to be visible. If they are perpendicular, however, the contrast between container 114 and the defect is enhanced.

Figure 4A:
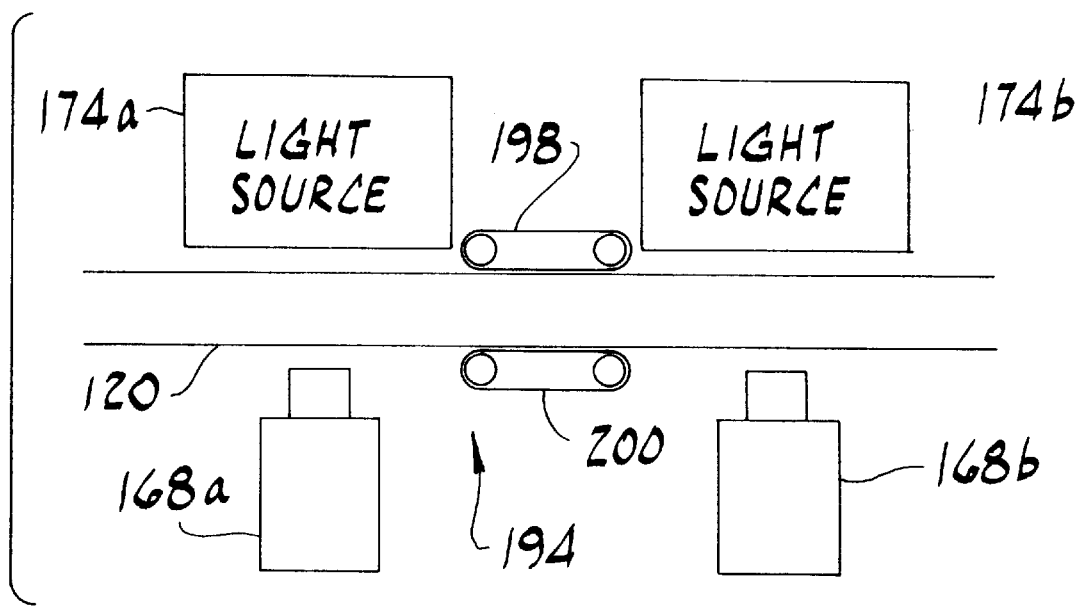
FIGS. 4A and 4B are diagrammatic views of preferred test configurations according to the embodiment of FIG. 3.
Figure 4B:
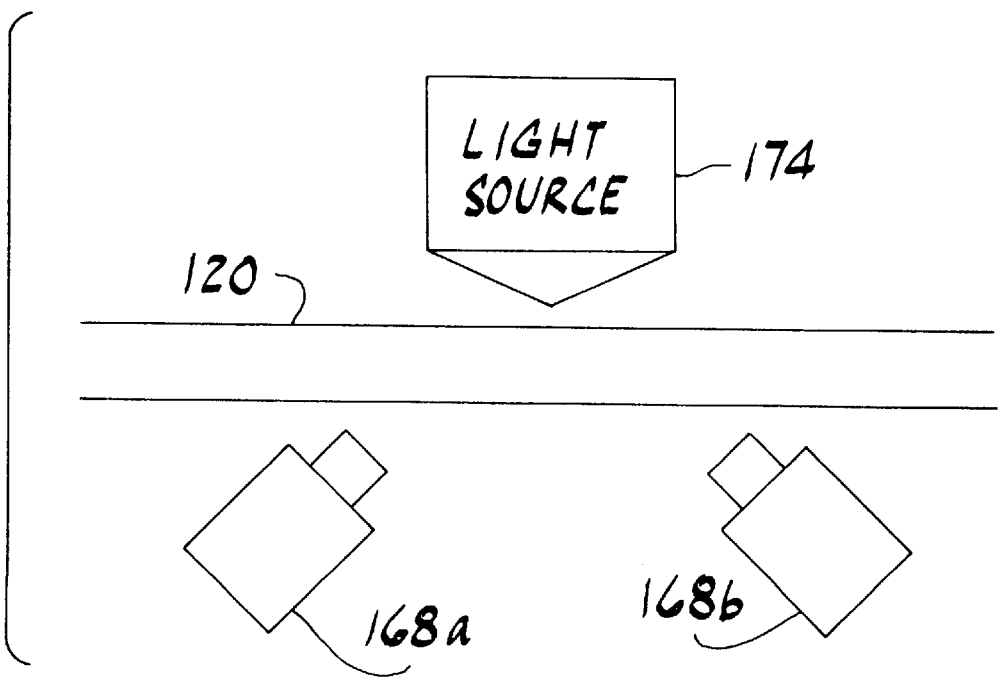

FIGS. 4A and 4B provide diagrammatic illustrations of the interior of inspection station 122 embodying the imaging configuration of FIG. 3. As shown in FIG. 4A, conveyor 120 moves containers 114 through the imaging area between a first camera 168a and a first light source 174a. A container transport assembly 194, also referred to as a container positioning or carry belt assembly, is adapted for rotating containers 114 as they move through inspection station 122. Conveyor 120 then moves containers 114 through the imaging area between a second camera 168b and a second light source 174b. As such, the first and second cameras 168a, 168b constitute first and second side wall inspections cameras, respectively.

In one preferred embodiment of the invention, the container transport assembly 194 includes motors (see FIG. 6) for driving a set of carry belts 198, 200. The carry belts 198, 200 engage the sides of containers 114 as they pass through inspection station 122 in a relatively straight-line path. Preferably, the motors drive carry belts 198, 200 independent of each other and sets the speed ratio between the two based on container diameter so that they rotate containers 114 approximately 90°. In one embodiment, encoder feedback from conveyor 120 enables an auto rotation feature for container transport assembly 194. This configuration provides the maximum contrast of stress-related defects while keeping conveyor space to a minimum. As such, container transport assembly constitutes a container rotator. It is contemplated that container transport assembly 194 may also be embodied by a turn-table, star wheel or other known container rotator for rotating containers 114 to provide at least two views of each container 114 under inspection.

In the alternative, FIG. 4B embodies an image configuration which also provides two views of each container 114. In this instance, the first camera 168*a* and the second camera 168*b* are mounted at 45° and 135° angles, respectively, relative to conveyor 120. As shown in FIG. 4B, conveyor 120 moves containers 114 through the imaging area between both first camera 168*a* and second camera 168*b* and a single light source 174. Thus, containers 114 are not subject to mechanical handling. However, more conveyor space and a greater separation between containers 114 may be used in this embodiment. By using cross polarizers on each side of containers 114 and special filtering combined with a diffused back lighting, the stress-related defects are optically enhanced. This technique minimizes the amount of unwanted light while passing off-axis light in the stress-related areas of containers 114.

Figure 5:
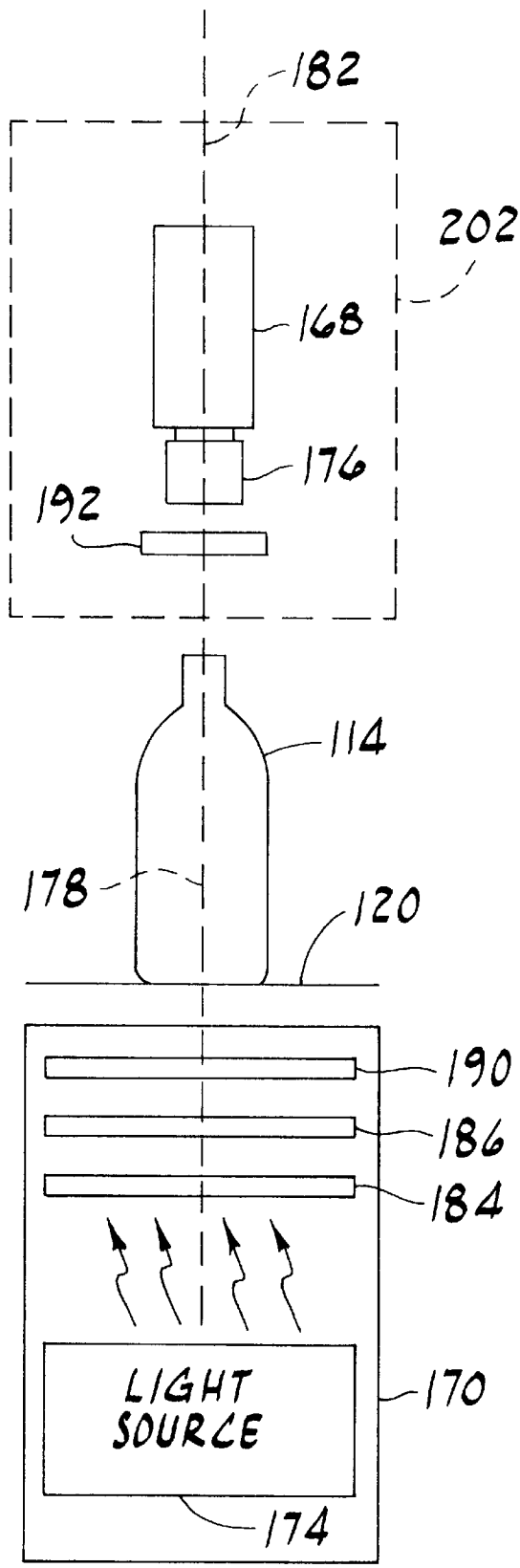
FIG. 5 is a diagrammatic view of a container to be inspected in an inspection station of the system of FIG. 1 according to another preferred embodiment of the invention.

Referring now to FIG. 5, another preferred electronic/optical imaging configuration for bottom stress detection includes diffuser/strobe assembly 170 positioned below container 114 and camera 168 positioned directly above it. Preferably, the vertical position of camera 168 may be adjusted to accommodate containers 114 of various heights. Although container 114 is shown in a vertical or upright orientation, it is to be understood that this orientation is merely illustrative. System 110 inspects containers 114 without regard to their orientation so long as the relationship between camera 168 and the bottom portions of containers 114 is generally the same.

In the embodiment of FIG. 5, diffuser/strobe assembly 170 constitutes a base adapted to receive at least one of the containers 114 handled by container handling apparatus 12. The base has a generally planar and level top surface over which container 114 is translated to allow illumination of its bottom portion. According to the invention, container handling apparatus 112 transports at least one container 114 to inspection station 122 via conveyor 120. Carry belts 198, 200 of container transport assembly 194 then move container 114 across the base for inspection. A mechanism, such as a star wheel, may also be included for carrying container 114 over light source 174 to inspect the bottom of container 114. In this instance, camera 168 generates the image of container 114 approximately when the axis of symmetry 178 of container 114 and the optical axis 182 of camera 168 are coaxial. In other words, camera 168 generates an image of container 114 when it is approximately centered below camera 168. Again, it is to be understood that the image of container 114 generated by camera 168 includes at least a portion of container 114 (e.g., a bottom portion) viewed from a particular angle.

Figure 6:
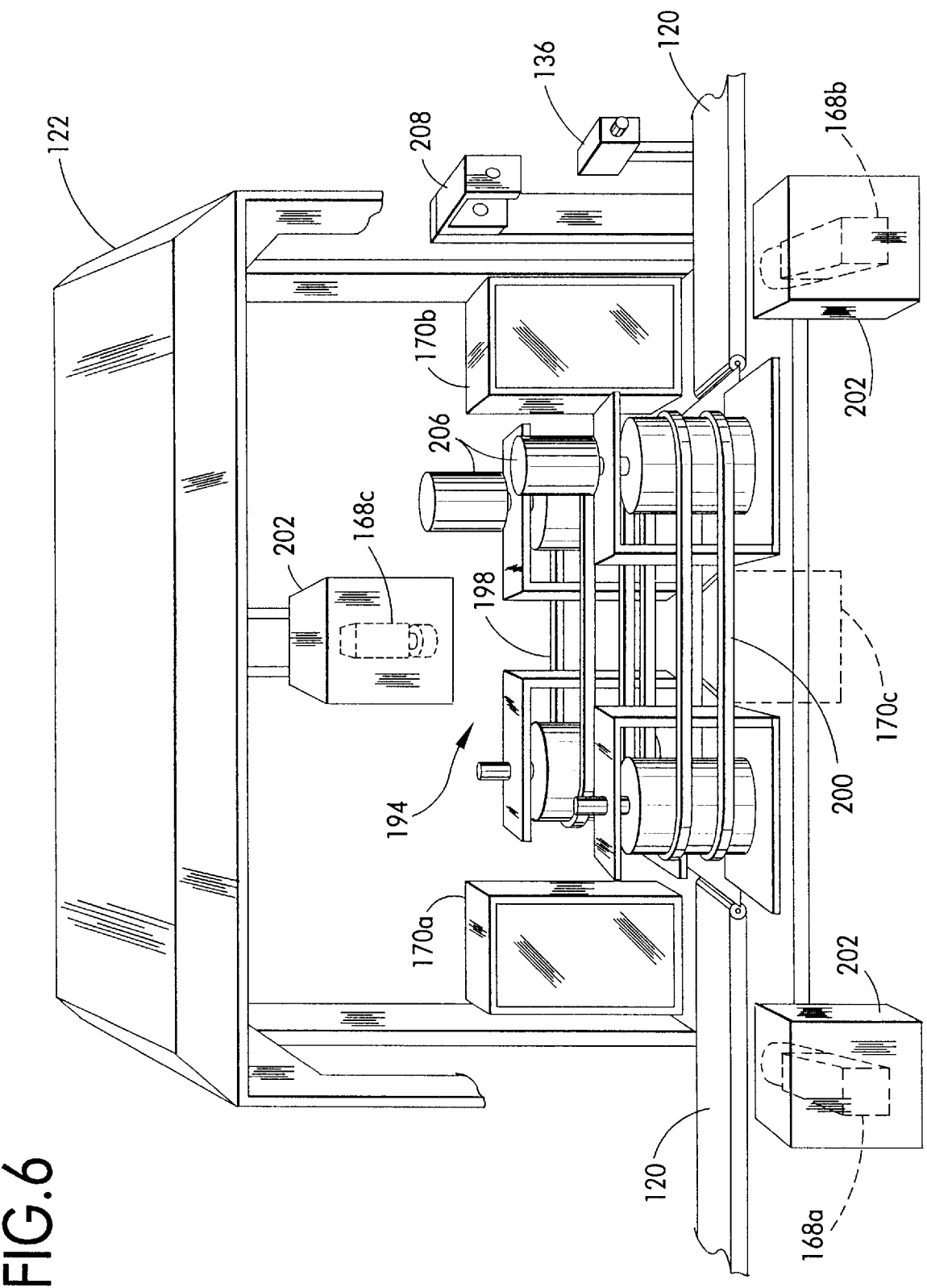
FIG. 6 is a perspective view of an inspection station of the system of FIG. 1 having portions broken away and illustrating a preferred test configuration according to the embodiment of FIG. 3 in combination with the embodiment of FIG. 5.

FIG. 6 is a perspective view of the interior of inspection station 122 embodying the imaging configuration of FIG. 3 in combination with the imaging configuration of FIG. 5. In this instance, each camera 168 is mounted in a camera box 202. Each camera box 202 positions and protects camera 168 and has a transparent window (not shown) through which the respective camera 168 views container 114. Conveyor 120 transports containers 114 through the imaging area between first camera 168*a* and first light source 174*a* (shown as part of a first diffuser/strobe assembly 170*a*). Container transport assembly 194 then moves and rotates containers 114 through inspection station 122. Conveyor 120 then transports containers 114 through the imaging area between second camera 168*b* and second light source 174*b* (shown as part of a second diffuser/strobe assembly 170*b*).

As shown in FIG. 6, a motor assembly 206 drives carry belts 198, 200. Carry belts 198, 200 engage the sides of containers 114 as they pass through inspection station 122 in a relatively straight-line path. Preferably, the motor assembly 206 drives carry belts 198, 200 independent of each other and sets the speed ratio between the two based on container diameter so that they rotate containers 114 approximately 90° in addition to moving them through the imaging area between a third camera 168*c* and a third light source 174*c* (shown as part of a third diffuser/strobe assembly 170*c*). In this instance, first camera 168*a* constitutes a side wall inspection camera and third camera 168*c* constitutes a bottom inspection camera.

System 110 preferably employs one or more position sensors (not shown) for initiating various stages of the inspection process. For example, top and/or bottom acquisition sensors may be used to detect the position of containers 114 relative to the field of view of cameras 168*a*, 168*b*, 168*c*. Camera 168*a* is responsive to at least one of the acquisition sensors for generating an image of container 114 in its imaging area. Cameras 168*c*, 168*b* are then responsive to other acquisition sensors or are triggered a delay interval after the container 114 under inspection passes camera 168*a*.

In one embodiment, the acquisition sensors used for container detection are photoelectric sensors employing fiber optic cables in a through-beam mode. Preferably, each sensor is located outside the field of view of the respective camera 168. Once container 114 breaks the beam of light provided by the sensor, a high speed counter clocked by an encoder mounted on conveyor 120, for example, starts counting. The encoder generates feedback signals representing the movement of conveyor 120, or carry belts 198, 200, which, in turn, further indicate the movement of container 114 within inspection station 122. Preferably, the high speed counter is loaded with an offset value to delay the image acquisition until container 114 is in the field of view of the respective camera 168. This counter can be implemented in hardware or software.

FIG. 6 also illustrates a rejector sensor 208 similar to the acquisition sensors for sensing the position of containers 114 as they travel out of inspection station 122. For example, if a particular container 114 fails inspection then rejector 136 receives an activating signal a fixed time (or travel distance) after the rejector sensor 208 sensed the presence of that container 114. Preferably, this fixed time is based on encoder clocking delay to handle varying speeds. Triggered by the activating signal, rejector 136 removes the defective container 114 from the line and deposits it on reject accumulation conveyor 138.

With respect to the inspection process, camera 168 preferably consists of an array of light sensors known as charge-coupled devices. The output of the sensors form an image with respect to their spatial location. Generally, spatial sampling of the sensors is analogous to superimposing a grid on the imaged portion of container 114 and examining the energy output from each grid box. Each spatial location in the image (or grid) is known as a picture element, or pixel. Computer 144 advantageously performs analog-to-digital conversion as shown in the data flow diagram of FIG. 7. As shown, a flash analog-to-digital converter 210 transforms the analog voltage to a digital value whereby a number, or pixel value, is assigned as a function of the amount of energy observed at each spatial location of the sensor array of each camera. Computer 144 assigns pixel values to the electrical signals from camera 168 to form a matrix of numbers, i.e., a digital representation of the image. The size of the sampling grid is given by the number of pixels on each side of the grid. For example, camera 168 resolves each image of container 114 into an array of 512×512 pixels. For each pixel, camera 168 produces an analog voltage signal that computer 144 converts to an 8-bit or longer digital value. In the alternative, if camera 168 produces a digital value, the flash A/D is omitted from the data flow diagram of FIG. 7 although some logic and level translation may be performed.

The process of sampling the output of the sensor array of camera 168 in a particular order is known as scanning and provides conversion of a two-dimensional energy signal, or image, to a one-dimensional electrical signal that can be processed by computer 144. Thus, as container handling apparatus 112 moves container 114 through inspection station 122, camera 168 and computer 144 cooperate to capture an image of container 114.

The digital values of the captured image are loaded into the memory 152 of computer 144 (e.g., a tri-port VRAM) for use by its CPU 150 and/or hardware processing logic. In a preferred embodiment, memory 152 stores the images generated by camera 168 as arrays of 512×512 pixels having 256 gray levels. Computer 144 then analyzes the gray level changes of the images stored in memory 152 to detect the presence of stress-causing defects. Computer 144 preferably defines window regions or areas of interest. With respect to the shape of the regions, it is to be understood that they may be of various shapes depending on the desired region to be examined. Thus, computer 144 constitutes an image processor for detecting an optical characteristic of the image within a defined region of the image.

Figure 7:
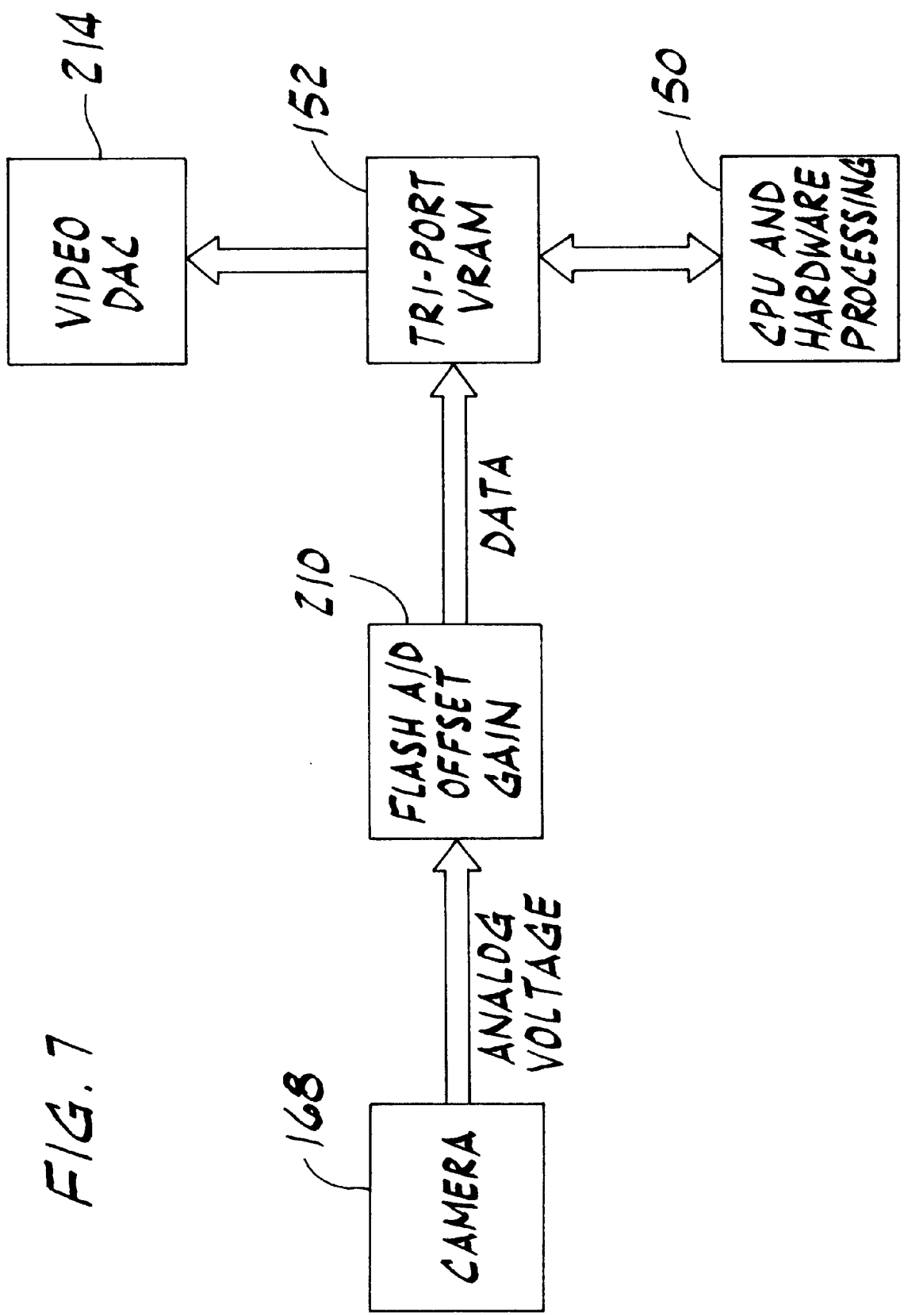
FIG. 7 is a block diagram illustrating data flow within the system of FIG. 1.

As shown in FIG. 7, a video digital-to-analog converter 214 of electronic control 142 has access to the stored data for displaying the image on monitor 154. Advantageously, an overlay may also be displayed on monitor 154 to highlight regions of interest or defects in the image.

Figure 8:
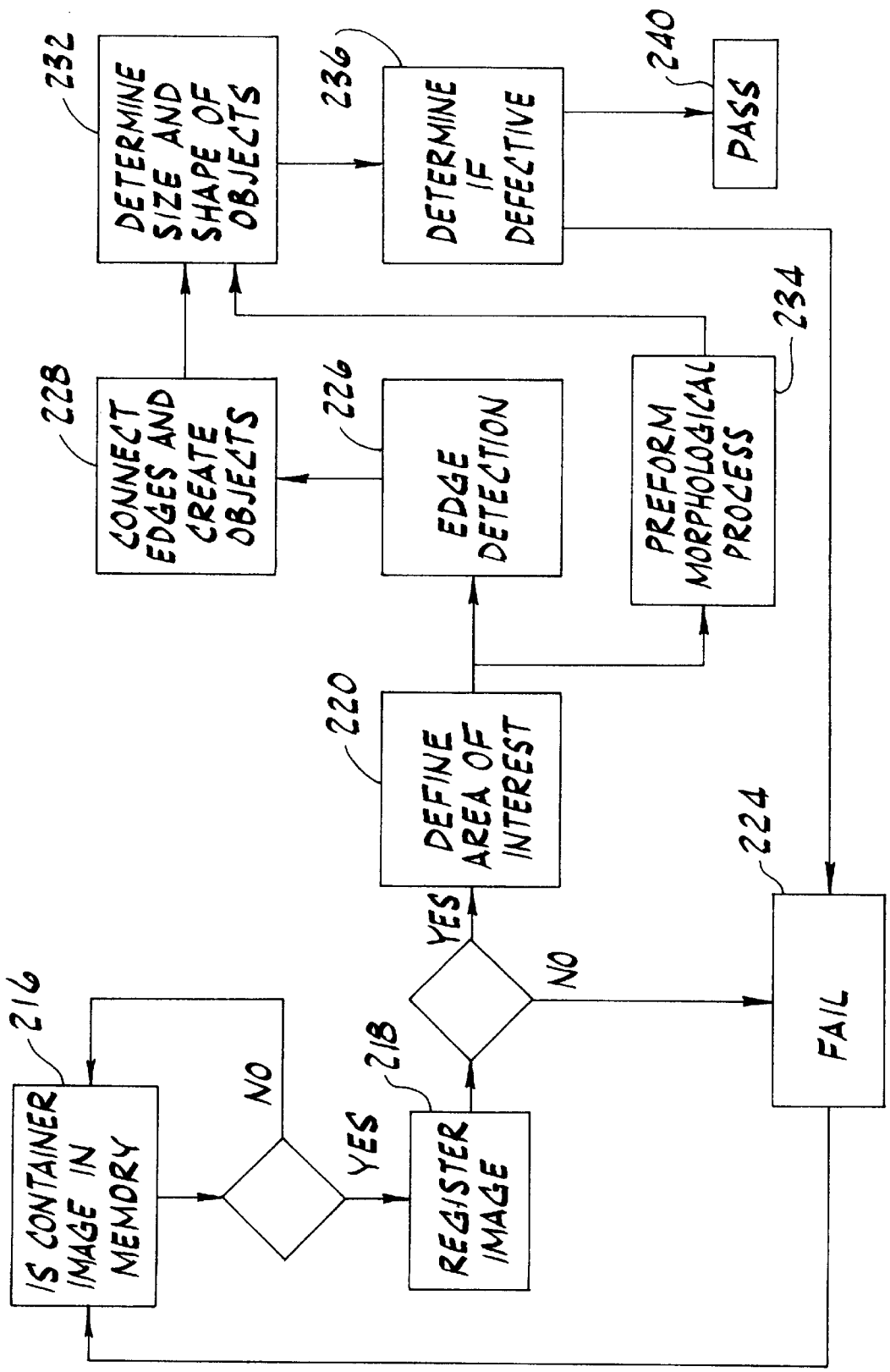
FIG. 8 illustrates an exemplary flow diagram of the operation of a computer of the system of FIG. 1.

FIG. 8 illustrates the image analysis process in the form of a flow diagram. As described above, camera 168 generates an image comprising a plurality of pixels, each pixel having a value representative of a detected optical characteristic of the image. In this instance, the pixel values correspond to the intensity of the pixels as represented by their gray levels. Beginning at step 216, computer 144 determines if an image is stored in its memory 152. If not, computer 144 repeats step 216. If an image is in memory 152, computer 144 proceeds to step 218 for registering the image. In other words, computer 144 locates container 114 in the image.

Figure 9A:
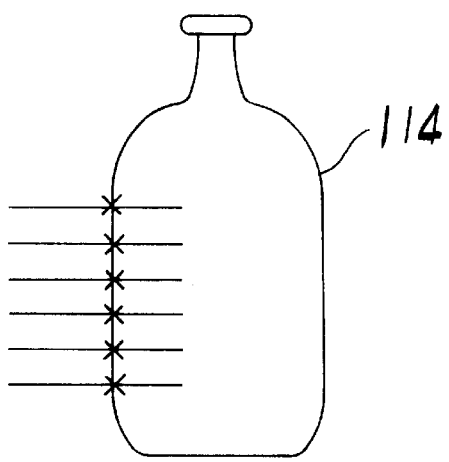
FIG. 9A is a side view of an exemplary container to be inspected by the system of FIG. 1 illustrating registration lines.
Figure 9B:
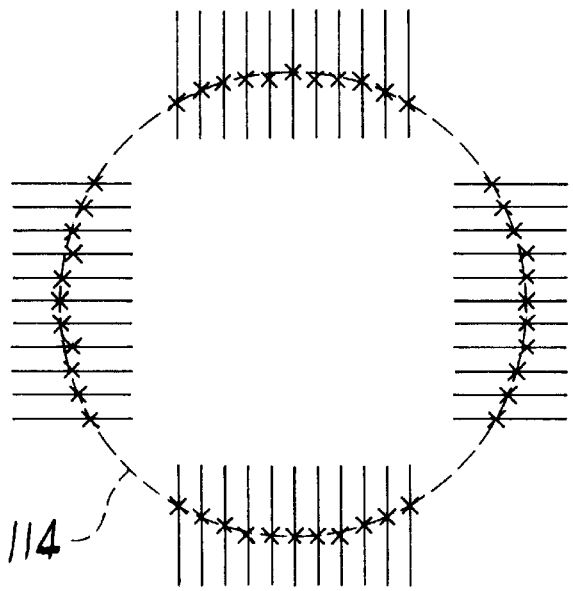
FIG. 9B is a bottom view of an exemplary container to be inspected by the system of FIG. 1 illustrating registration lines.

FIGS. 9A and 9B each illustrate an exemplary registration of a captured image of container 114. In general, registration is used to locate container 114 in the memory array stored in memory 152 for accurate placement of zones or areas of interest for inspection. For example, FIG. 9A shows registration lines on an image for detecting a side wall portion of container 114 and FIG. 9B shows registration lines on an image for detecting the center of a bottom portion of container 114. Computer 144 scans the pixels of the image along the registration lines and performs convolution or another edge operator to detect edges of container 114. Each edge detected during the registration process is indicated by an X on the registration lines of FIGS. 9A and 9B. Preferably, the registration, or scan, lines are directional (e.g., scanning from inside to outside or vice versa). In the case of FIG. 9B, computer 144 calculates the approximate center of the bottom of container 114 based on the location of the detected edges.

Figure 10A:
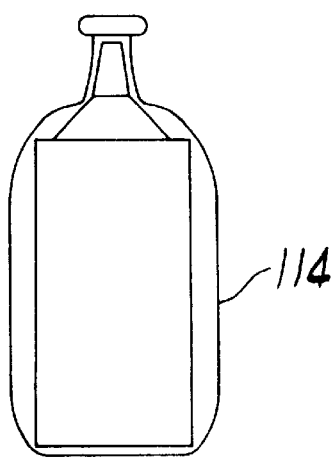
FIG. 10A is a side view of an exemplary container to be inspected by the system of FIG. 1 illustrating defined areas of interest.
Figure 10B:
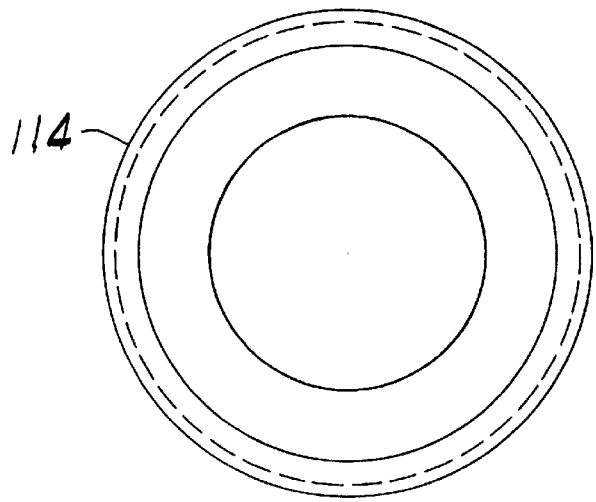
FIG. 10B is a bottom view of an exemplary container to be inspected by the system of FIG. 1 illustrating defined areas of interest.

After registration of the image at step 218 of FIG. 8, computer 144 proceeds to step 220 for defining areas of interest by placing zones on container 114 as shown in FIGS. 10A and 10B. These zones are accurately placed on container 114 by using the edge data from registration. By using multiple zones, the user has full flexibility of defining particular problem areas on container 114. Each zone can have multiple algorithms to find edges as well as multiple sensitivities and sizing. For example, zones of interest can be placed on the bottom of container 114 as shown in FIG. 10B to allow flexible inspection through the bottom. This may be based on decoration in the bottom or customer requirements. Preferably, computer 144 defines the position of the zones by x and y movement as well as inside and outside diameter.

Referring further to FIG. 8, if container 114 is not found in the image at step 218, computer 144 fails the imaged container 114 at step 224 and returns to the beginning at step 216.

After computer 144 defines the zones of interest at step 220, computer 144 proceeds to step 226 for performing edge detection within the defined zones. In the vision system arts, edges are defined as regions in the image where there is a relatively large change in gray level over a relatively small spatial region. According to the invention, computer 144 performs several routines for analyzing the image, including edge detection routines that analyze the gray level changes in the defined window regions for detecting the presence of marks. Various edge detection operators, or algorithms, for finding and counting edges in an image are known to those skilled in the art. For example, suitable edge detection routines include Sobel or Prewit algorithms.

In the edge detection step, computer 144 examines each of the pixels in the defined region one at a time with respect to the pixels surrounding the pixel under examination. In one embodiment, computer 144 begins with the upper left corner of the (x,y) coordinate system, examines each pixel in the top row from left to right, and then moves down to the next row. Computer 144 then repeats its examination for the next row. It is to be understood, however, that a different originating position may be selected or a different scanning technique employed. For example, computer 144 first determines the row number of the pixel being examined. In this instance, the pixel under examination, i.e., the pixel at the current row and column number, is designated pixel E and is at the center of a three-by-three matrix of pixels:

$$
\begin{matrix} A & B & C \\ D & E & F \\ G & H & I \end{matrix}
$$

The matrix of pixels is also referred to as a kernel, template or structuring element. If the pixel's row number is less than the total number of rows, the edge detection routine continues because computer 144 has not yet examined each of the pixels in the region.

Likewise, computer 144 determines the column number of the pixel being examined, i.e., pixel E. As before, if the column number of pixel E is less than the total number of columns, which it will be beginning with column=0, the edge detection routine continues because computer 144 has not yet examined each of the pixels in the region. Computer 144 then determines the gradient for pixel E as a function of the pixel values of the surrounding pixels. Merely as an example, GRADIENT=(A+2D+G)−(C+2F+I). It is to be understood that a different gradient formula may be used. Computer 144 compares the determined gradient to a threshold for finding edges.

Computer 144 continues for each of the pixels in the defined region.

In a preferred embodiment of the invention, computer 144 then performs connectivity analysis at step 228 to group the detected edges in the image as a function of, for example, their coordinates. In this manner, computer 144 defines objects, or marks, in the image. It is to be understood that in addition to intensity or intensity gradient, other characteristics of the image, such as color or contrast, may be used to optically distinguish objects in the image of container 114. After grouping the edges, computer 144 determines the size and shape of the detected objects at step 232. According to one grouping technique, the defined objects are described by a bounding box and their (x,y) positions. For example, the bounding box is the smallest rectangle that would enclose a regular-shaped object and, thus, is indicative of the object's size. In the alternative, the defined objects may be described by blob analysis, by examining the shape of the object (e.g., the ratio of the object's major and minor axes) or by examining the area of the object.

The object labeling step is similar to the edge detection routine in that computer 144 first determines the row number and then column number of the pixel being examined (i.e., pixel E) and continues until each of the pixels in the entire region of interest is examined.

As an example of an object labeling routine, computer 144 first determines whether pixel E is defined to be an edge. If so, it determines if any of the surrounding pixels are already labeled. For example, computer 144 determines if pixels D, A, B or C are labeled. If none of these pixels are already labeled, computer 144 assigns a unique label to pixel E. If, on the other hand, at least one of pixels D, A, B or C already has a unique label, computer 144 labels pixel E with the same label previously assigned to the first pixel in the sequence of pixels D, A, B and C. For example, if pixel E is an edge, pixels B and C are labeled and pixels D and A are not labeled, then pixel E will be assigned the same label as pixel B. The other labels for the pixels in this sequence are then set to pixel E's label. In the example, pixels E, B and C will all have the same label. Following this step in the object labeling routine, computer 144 returns to the next column.

In addition, computer 144 executes a preform morphological process at step 234 for use in determining at step 232 the size and shape of the detected objects. Following step 232, computer 144 executes various inspection routines at step 236 to inspect container 114 for defects or undesirable production trends as a function of the size, shape and location of the detected objects. Preferably, computer 144 executes different inspection algorithms which are suited for detection of different types of defects. If computer 144 determines that container 114 is defective, it fails at step 224. Otherwise, container 114 passes inspection at step 240.

In one embodiment, each inspection zone can have several test categories assigned at the same time. The tests assigned to a zone can be all different, or they can be of the same category with different parameters. One such test involves analyzing a strip average for variations in pixel intensity between average values of pixels along a strip. Other tests involve either scanning to detect edges in the image where defects are defined by the number of detected edges within a given area. Another test involves analyzing a histogram of the gray values within the defined region. Essentially, the histogram is a density analysis of the gray levels. In this instance, defects are defined by a peak in the histogram falling outside a user-defined range.

Also, system 110 may be used in combination with, for example, a weight station, pushup measuring system, bottom inspection station, mold number reading system, and/or optical profile measuring apparatus for further inspection. U.S. Pat. No. 4,906,098, the entire disclosure of which is incorporated herein by reference, discloses one preferred embodiment of optical profile measuring apparatus and commonly assigned patent application Ser. No. 08/534,496, filed Sep. 27, 1995, the entire disclosure of which is incorporated herein by reference, discloses a preferred pushup sensor. A suitable companion inspection system for container bottoms is the Superscan II, manufactured by BWI Inex Vision Systems, 13327 U.S. Highway 19 North, Clearwater, Fla. 34624.

Other inspection systems, measuring devices, and improvements for such are disclosed in U.S. Pat. No. 4,082,463, U.S. Pat. No. 4,074,938, and U.S. Pat. No. 4,097,158, the entire disclosures of which are also incorporated herein by reference. U.S. Pat. No. 4,082,463 shows a calibrated optical micrometer and U.S. Pat. No. 4,074,938 shows an optical dimension measuring device employing an elongated, focused beam. U.S. Pat. No. 4,097,158 shows a half-maximum threshold circuit for an optical micrometer.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A system for inspecting a container for stress defects comprising:

a light source for providing light to illuminate the container;

a camera for generating an image of the illuminated container, said image including a plurality of pixels, said pixels each having a value representative of an optical characteristic of the image;

a first polarizer positioned between the light source and the container for polarizing the light illuminating the container;

a second polarizer positioned between the container and the camera for polarizing the light transmitted through the container to the camera, said first and second polarizers each having an axis of transmission, said axes of transmission being non-parallel relative to each other; and an image processor for processing the image generated by the camera, said image processor:

scanning the image as a function of the pixel values to acquire edge data by which a portion of the container is identified in the image;

defining at least one region of interest in the image, said defined region having a size, shape and position based on the container portion identified in the image; and inspecting the image as a function of the pixel values within the defined region to detect edges in the image which correspond to defects in the container.

2. The system of claim 1 wherein the axis of transmission of the first polarizer is approximately perpendicular to the axis of transmission of the second polarizer.

3. The system of claim 1 further comprising a diffuser for diffusing the light provided by the light source.

4. The system of claim 1 further comprising a light control filter for filtering the light provided by the light source to reduce glare from the illuminated container.

5. The system of claim 1 wherein the camera comprises a first camera and further comprising a second camera for generating another image of the illuminated container, a third polarizer for polarizing the light illuminating the container and a fourth polarizer for polarizing the light transmitted through the container to the second camera, said third and fourth polarizers each having an axis of transmission, said axes of transmission being non-parallel relative to each other.

6. The system of claim 5 wherein the first and second cameras each have an optical axis, said optical axes being non-parallel relative to each other.

7. The system of claim 6 wherein the optical axis of the first camera is generally perpendicular to an axis of symmetry of the container and wherein the optical axis of the second camera is generally parallel to the axis of symmetry of the container.

8. The system of claim 5 further comprising a container rotator for rotating the container before the second camera generates the other image of the illuminated container.

9. The system of claim 1 wherein the image processor groups the detected edges as a function of their locations in the image to define objects in the image, said defined objects each including one or more pixels, and wherein the image processor includes a memory storing information regarding defects as a function of the defined objects.

10. The system of claim 1 wherein the pixel values correspond to the intensity of the pixels and wherein the optical characteristic of the image detected by the image processor is a gradient of the pixel values.

11. The system of claim 10 wherein the image generated by the camera includes an image of the bottom of the container and the defined region is approximately centered on the image of the bottom of the container.

12. The system of claim 11 wherein the defined region has a generally circular periphery and an outer radius corresponding to the size of the container.

13. The system of claim 1 wherein the container has an axis of symmetry and the camera has an optical axis and further comprising a position sensor for detecting the position of the container relative to the camera, said camera being responsive to the position sensor for generating the image of the container approximately when the axis of symmetry of the container intersects the optical axis of the camera.

14. The system of claim 13 wherein the camera is responsive to the position sensor for generating the image of the container when the axis of symmetry of the container is generally coaxial with the optical axis of the camera.

15. The system of claim 1 for use with a lehr for annealing the container before inspection by the system, further comprising a feedback circuit for providing information representative of the detected defects, said lehr being controlled as a function of the information provided by the feedback circuit so that the defects may be corrected in containers subsequently annealed in the lehr.

16. The system of claim 1 for use with a container molding apparatus for forming the container, further comprising a feedback circuit for providing information representative of the detected defects, said container molding apparatus being controlled as a function of the information provided by the feedback circuit so that the defects may be corrected in containers subsequently formed by the container molding apparatus.

17. The system of claim 1 for use with another inspection apparatus for inspecting the container for defects, further comprising a feedback circuit for providing information representative of the detected defects from the system to the other inspection apparatus, said other inspection apparatus being controlled as a function of the information provided by the feedback circuit.

18. The system of claim 1 wherein the image processor defines a plurality of regions of interest in the image based on the size and shape of the container and wherein the image processor executes an edge detection routine for detecting edges in the image within one region of interest and executes a different edge detection routine for detecting edges in the image within another region of interest.

19. A method of inspecting a container for stress defects comprising:
    positioning the container between a light source and a camera;
    positioning a first polarizer between the light source and the container;
    positioning a second polarizer between the container and the camera, said first and second polarizers each having an axis of transmission, said axes of transmission being non-parallel relative to each other;
    illuminating the container with light provided by the light source;
    polarizing the light illuminating the container with the first polarizer;
    polarizing the light transmitted through the container to the camera with the second polarizer;
    generating an image of the container with the camera, said image including a plurality of pixels, said pixels each having a value representative of an optical characteristic of the image;
    scanning the image as a function of the pixel values to acquire edge data by which a portion of the container is identified in the image;
    defining at least one region of interest in the image, said defined region having a size, shape and position based on the container portion identified in the image; and
    processing the image as a function of the pixel values within the defined region to detect edges in the image which correspond to defects in the container.

20. The method of claim 19 wherein the steps of positioning the first and second polarizers includes positioning the axis of transmission of the first polarizer approximately perpendicular to the axis of transmission of the second polarizer.

21. The method of claim 19 further comprising the step of diffusing the light provided by the light source.

22. The method of claim 19 further comprising the step of filtering the light provided by the light source to reduce glare from the illuminated container.

23. The method of claim 19 further comprising the steps of polarizing the light illuminating the container with a third polarizer, polarizing the light transmitted through the container to a second camera with a fourth polarizer, and generating another image of the illuminated container with the second camera.

24. The method of claim 23 wherein each of the cameras has an optical axis and further comprising the step of positioning the cameras so that the optical axes are nonparallel relative to each other.

25. The method of claim 24 further comprising the step of positioning the cameras so that the optical axis of one of the cameras is generally perpendicular to an axis of symmetry of the container and the optical axis of the other camera is generally parallel to the axis of symmetry of the container.

26. The method of claim 23 further comprising the step of rotating the container before generating the other image of the illuminated container with the second camera.

27. The method of claim 19 further comprising the step of grouping the detected edges as a function of their locations in the image to define objects in the image, said defined objects each including one or more pixels, and the steps of storing information regarding defects in a memory and retrieving the stored information from the memory as a function of the defined objects.

28. The method of claim 19 wherein the pixel values correspond to the intensity of the pixels and wherein the step of detecting an optical characteristic of the image comprises detecting a gradient of the pixel values.

29. The method of claim 19 wherein the image generated by the camera includes an image of the bottom of the container and further comprising the step of approximately centering the defined region on the image of the bottom of the container.

30. The method of claim 29 wherein the step of defining the region includes defining a region having a generally circular periphery and an outer radius corresponding to the size of the container.

31. The method of claim 19 wherein the container has an axis of symmetry and the camera has an optical axis and further comprising the step of detecting the position of the container relative to the camera, said camera being responsive to the detected position for generating the image of the container approximately when the axis of symmetry of the container intersects the optical axis of the camera.

32. The method of claim 31 wherein the step of generating the image includes generating the image when the axis of symmetry of the container is generally coaxial with the optical axis of the camera.

33. The method of claim 19 for use with a lehr for annealing the container before inspection, further comprising the steps of providing information representative of the detected defects in the container and controlling the lehr as a function of the information so that the defects may be corrected in containers subsequently annealed in the lehr.

34. The method of claim 19 for use with a container molding apparatus for forming the container, further comprising the steps of providing information representative of the detected defects in the container and controlling the container molding apparatus as a function of the information so that the defects may be corrected in containers subsequently formed by the container molding apparatus.

35. The method of claim 19 for use with another inspection apparatus for inspecting the container for defects, further comprising the steps of providing information representative of the detected defects in the container to the other inspection apparatus and controlling the other inspection apparatus as a function of the information.

36. The method of claim 19 wherein the defining step comprises defining a plurality of regions of interest in the image based on the size and shape of the container and further comprising the step of executing an edge detection routine for detecting edges in the image within one region of interest and executing a different edge detection routine for detecting edges in the image within another region of interest.

* * * * *